US010463623B2

(12) United States Patent
Pilgaonkar et al.

(10) Patent No.: US 10,463,623 B2
(45) Date of Patent: Nov. 5, 2019

(54) COMPOSITIONS EXHIBITING DELAYED TRANSIT THROUGH THE GASTROINTESTINAL TRACT

(75) Inventors: Pratibha Sudhir Pilgaonkar, Mumbai (IN); Maharukh Tehmasp Rustomjee, Mumbai (IN); Anilkumar Surendrakumar Gandhi, Mumbai (IN); Rupali Kedar Suvarnapathaki, Mumbai (IN)

(73) Assignee: RUBICON RESEARCH PRIVATE LIMITED, Mumbai (IN)

( * ) Notice: Subject to any disclaimer, the term of this patent is extended or adjusted under 35 U.S.C. 154(b) by 365 days.

(21) Appl. No.: 13/120,288

(22) PCT Filed: Sep. 22, 2009

(86) PCT No.: PCT/IN2009/000516
§ 371 (c)(1),
(2), (4) Date: Jun. 6, 2011

(87) PCT Pub. No.: WO2010/038237
PCT Pub. Date: Apr. 8, 2010

(65) Prior Publication Data
US 2011/0229569 A1    Sep. 22, 2011

(30) Foreign Application Priority Data
Sep. 22, 2008  (IN) .................. 2020/MUM/2008

(51) Int. Cl.
*A61K 9/24* (2006.01)
*A61K 9/20* (2006.01)
*A61K 36/48* (2006.01)
*A23L 33/22* (2016.01)
*A61K 47/46* (2006.01)

(52) U.S. Cl.
CPC .............. *A61K 9/209* (2013.01); *A23L 33/22* (2016.08); *A61K 9/2068* (2013.01); *A61K 36/48* (2013.01); *A61K 47/46* (2013.01); *A23V 2002/00* (2013.01)

(58) Field of Classification Search
CPC ............ A23V 2002/00; A23V 2200/32; A23V 2200/3202; A23V 2250/032; A23V 2250/242; A23V 2250/2482; A23V 2250/264; A23V 2250/51082; A23V 2250/51084; A23V 2250/612; A61K 36/48; A61K 47/46; A61K 9/2068; A61K 2300/00; A61K 9/0014; A61K 9/006; A61K 9/0095; A61K 9/1664; A61K 9/288; A61K 9/7007; A61K 8/737; A61K 8/97; A61K 9/209; C08L 2666/26; C08L 1/04; C08L 5/00; C08L 2205/16; A23L 33/22; A23L 25/30; A23L 29/238; A23L 33/105; A23L 33/21; A23L 7/117; A23C 9/1544; A23G 3/42; A23G 9/34; A23G 9/42; A61Q 19/00; C08B 37/0087; C11D 3/222
See application file for complete search history.

(56) References Cited

U.S. PATENT DOCUMENTS

| | | | |
|---|---|---|---|
| 5,997,877 A | 12/1999 | Chang | |
| 6,340,475 B2 | 1/2002 | Shell et al. | |
| 6,635,280 B2 | 10/2003 | Shell et al. | |
| 9,295,643 B2 * | 3/2016 | Pilgaonkar | A61K 9/0014 |
| 2001/0043946 A1* | 11/2001 | Vilkov | 424/465 |
| 2003/0104053 A1 | 6/2003 | Gusler et al. | |
| 2004/0219186 A1 | 11/2004 | Ayres | |
| 2004/0228932 A1* | 11/2004 | Pilgaonkar et al. | 424/757 |
| 2005/0084549 A1* | 4/2005 | Pilgaonkar et al. | 424/757 |
| 2005/0158380 A1* | 7/2005 | Chawla et al. | 424/465 |
| 2006/0177497 A1 | 8/2006 | Hoikhman et al. | |
| 2006/0269626 A1 | 11/2006 | Martinez | |
| 2007/0128276 A1 | 6/2007 | Jain et al. | |

FOREIGN PATENT DOCUMENTS

| | | |
|---|---|---|
| DE | 3225056 | 1/1984 |
| EP | 0775451 | 5/1997 |
| EP | 1697050 | 10/2007 |
| EP | 1859786 | 11/2007 |
| EP | 1745775 | 5/2008 |
| GB | 2324725 | 11/1998 |
| WO | 92/18143 | 10/1992 |
| WO | 2005/009453 | 2/2005 |
| WO | 2009/057125 | 5/2009 |

OTHER PUBLICATIONS

Klausner et al. Expandable Gastroretentive Dosage Forms; Journal of Controlled Release 90 (2003) 143-162.*
Shirani et al. Extruded Products With Fenugreek (*Trigonella foenum-graecium*) Chickpea and Rice: Physical Properties, Sensory Acceptability and Glycaemic Index; Journal of Food engineering 90 (2009) pp. 44-52.*
Wikipedia: Polyvinylpyrrolidone; Online, URLhttp://en.wikipedia.org/wiki/Polyvinylpyrrolidone accessed Sep. 16, 2013, 5 pages.*
Mathur et al. Fenugreek and Other Lesser Known Legume Galactomannan-Polysaccharides: Scope for Developments; Journal of Scientific & Industrial Research, vol. 64, Jul. 2005, pp. 475-481.*
Rathee et al. Gastroretentive Drug Delivery Systems: A Review of Formualtion Approaches; IC Journal No. 7725vol. 1, No. 8, 2012, pp. 79-107.*
Sarojini et al. An Overview on Various Approaches to Gastroretentive Dosage Forms; International journal of Drug Development and Research, Jan.-Mar. 2012, 4 (1): 01-13.*
Sharma et al. Gastroretentive Drug Delivery System—A Mini Review; Asian Pac. J Health Sci 2014; 1(2): 80-89.*

(Continued)

*Primary Examiner* — Aaron J Kosar
(74) *Attorney, Agent, or Firm* — Blank Rome LLP

(57) ABSTRACT

The present invention provides a composition exhibiting delayed transit through the gastrointestinal tract comprising one or more active agents, fenugreek fiber and at least one pharmaceutically acceptable excipient. The present invention further relates to gastroretentive dosage forms comprising fenugreek fibers.

13 Claims, No Drawings

(56) References Cited

OTHER PUBLICATIONS

Patent Cooperation Treaty, "International Search Report," European Patent Office, in PCT Application No. PCT/IN2009/000516; Document of 4 pages, dated Jul. 14, 2010.
Patent Cooperation Treaty, "Written Opinion of the International Search Authority," European Patent Office, in PCT Application No. PCT/IN2009/000516; Document of 6 pages, dated Jul. 14, 2010.
Sharma et al., Effect of Fenugreek Seeds and Leaves on Blood Glucose and Serum Insulin Responses in Human Subjects, Nutrition Research, vol. 6, pp. 1353-1364, (Jan. 1, 1986).
Sharma et al., Hypoglycaemic Effect of Fenugreek Seeds in Non-Insulin Dependent Diabetic Subjects, Nutrition Research, vol. 10, pp. 731-739, (Jan. 1, 1990).
Garti et al., Fenugreek gum. The Magic Fiber for an Improved Glucose Response and Cholesterol Reduction, Nutrition, vol. 1, No. 3, pp. 5-10 (May 1, 2001).
Kumar et al., Fenugreek Dietary Fibre a Novel Class of Functional Food Ingredient, Agro Food Industry Hi-Tech, Tekno Science, IT, vol. 19, No. 2, pp. 18-21 (Mar. 31, 2008).

\* cited by examiner

COMPOSITIONS EXHIBITING DELAYED TRANSIT THROUGH THE GASTROINTESTINAL TRACT

CROSS REFERENCE TO RELATED APPLICATIONS

This application is a § 371 National Phase of PCT/IN2009/000516, filed Sep. 22, 2009, which claims priority to Indian Patent Application No. 2020/MUM/2008, filed Sep. 22, 2008, the entirety of both of which are herein incorporated by reference.

FIELD OF THE INVENTION

The present invention relates to compositions exhibiting delayed transit through the gastrointestinal tract comprising fenugreek fibers. The present invention also provides processes for preparing such compositions and methods of using such compositions.

BACKGROUND OF THE INVENTION

Despite tremendous advancements in drug delivery oral route remains the preferred route of administration for therapeutic agents because of low cost of therapy and ease of administration leading to high levels of patient compliance. A number of oral delivery systems have been developed which act as drug reservoirs from which the active substance can be released over a defined period of time at a predetermined and controlled rate. Such systems reduce dosage frequency, resulting in increased patient compliance. However, the conventional controlled release drug delivery systems have limited use in instances such as (1) drugs having an absorption window in the gastrointestinal tract; (2) local treatment of proximal parts of the gastrointestinal tract (stomach and/or duodenum); (3) drugs which degrade or are unstable in the intestinal/colonic environment; (4) drugs that exhibit low solubility at high pH values; and (5) drugs requiring a longer duration in the intestine.

All therapeutic agents are not absorbed uniformly throughout the gastrointestinal tract. Some drugs are absorbed from a particular portion of the gastrointestinal tract or are absorbed to a different extent in various segments of gastrointestinal tract. Such active agents are said to have an "absorption window". Thus, only the drug substance released in the region preceding and in close vicinity of the absorption window is available for absorption. After crossing the absorption window, the released drug substance will show very little or no absorption. This phenomenon drastically limits the success of a delivery system and, therefore, has led to the development of oral controlled release dosage forms exhibiting delayed transit through gastrointestinal tract. Such a dosage form can possess gastrointestinal retention capabilities and can hold these active agents near their absorption window for extended time periods, thereby achieving controlled release and/or improved bioavailability of the active ingredient.

Further, dosage forms with increased gastric residence time are advantageous for local action in the stomach and the upper part of the small intestine, for example treatment of peptic ulcer disease. Further, drugs which degrade or are unstable in the colonic/intestinal environment or exhibit low solubility at high pH values can be delivered to the upper gastrointestinal tract effectively via gastroretentive drug delivery systems. Overall maximized absorption of such therapeutic agents can be achieved by increasing the gastrointestinal retention time of the controlled release dosage form in the gastrointestinal tract, thus providing a constant stream of supply of the therapeutic agent for improved drug bioavailability benefits.

The gastrointestinal retention of solid dosage forms may be achieved by various mechanisms, such as mucoadhesion, flotation, sedimentation, swelling and expansion, or by the simultaneous administration of pharmacological agents which delay gastric emptying. Mucoadhesion relates to adhesion of the polymer utilized in the delivery system to the gastrointestinal mucus layer until it is removed spontaneously from the surface. Various physiological factors such as peristalsis, mucin turnover rate, gastrointestinal pH, fast/fed state and type of foods affect the degree of mucoadhesion. The mechanism of mucoadhesion is thought to be through the formation of electrostatic and hydrogen bonding at the polymer-mucus boundary. Generally, mucoadhesion is achieved with polymers having affinity for gastrointestinal mucosa and selected from a group comprising polycarbophils, carbomers, alginates, chitosan, gums, lectins, cellulose and cellulose derivatives or mixtures thereof.

Floatation as a retention mechanism works in cases wherein the delivery system has a bulk density lower than gastric fluid and remains buoyant in the stomach. These buoyant systems generally utilize matrices prepared with swellable polymers or polysaccharides and effervescent couples, e.g., sodium bicarbonate and citric or tartaric acid or matrices containing chambers of entrapped air or liquids that gasify at body temperature. In case of sedimentation or densification as a mechanism for gastroretention, the dosage form has high bulk density compared to the density of gastric contents. Such systems usually multiparticulates are retained in the rugae or folds of the stomach near the pyloric region and tend to withstand the peristaltic movements of the stomach wall. Further, these high density particles are also shown to significantly prolong the intestinal transit time.

Swelling and expansion is a potentially reliable retention mechanism wherein on swallowing the dosage form swells to an extent that prevents exit from the stomach through the pylorus. As a result, the dosage form is retained in the stomach for a long period of time. These systems are referred as 'plug type system' since they exhibit tendency to remain lodged at the pyloric sphincter. These dosage forms are excluded from the passage of the pyloric sphincter as they exceed a diameter of approximately 10-12 mm in their swollen or expanded state. The concept of simultaneous administration of a drug to delay gastric emptying together with a therapeutic active due to unfavorable response from clinicians and regulatory agencies because of the questionable benefit-to-risk ratio associated with their usage have been employed in a limited way.

Many researchers have developed gastroretentive drug delivery systems based on any one or a combination of the above mentioned mechanisms. The specific use of mucoadhesive formulations in the treatment of gastric disorders (including H. pylori) has been described in PCT Publication 92/18143. Prolonged gastric retention and sustained release is achieved by use of bioadhesive materials like natural gums and plant extracts and synthetic materials such as sucralfate, cellulose derivatives, acrylic acid and methacrylic acid derivatives, for example cross-linked acrylic and methacrylic acid copolymers available under the Trade Names CARBOPOL and POLYCARBOPHIL. GB Patent Application 2324725A1 highlights a pharmaceutical composition suitable for forming a mucoadhesive lining in the gastrointestinal tract comprising a particular form of alginic acid or alginate salt characterised in that the mannuronic acid:glucoronic acid residue ratio (M/G) is at least unity and effective to provide a bioadhesive interaction with the mucosa. U.S. Patent Application 20070128276A1 emphasizes a controlled release composition comprising nimesulide as an active agent formulated as a gastroretentive system. Herein mucoadhesion is achieved by treating nimesulide with polymers having affinity for gastrointestinal mucosa selected from a group comprising polycarbophils, carbomers, alginates, cellulose and cellulose derivatives, chitosan, gums, lectins, or mixtures thereof.

Many attempts have also been made to devise extended release gastroretentive drug delivery systems wherein the dosage form is small enough to ingest but is then retained after swelling in the gastro-intestinal area for a long enough time for the active agent to be released and eventually absorbed.

U.S. Patent Application 20030104053A1 discloses unit dosage form tablets for the delivery of pharmaceuticals wherein the active is dispersed in a solid unitary matrix that is formed of a combination of poly (ethylene oxide) and hydroxypropyl methylcellulose. This combination is said to offer unique benefits in terms of release rate control and reproducibility while allowing both swelling of the tablet to effect gastric retention and gradual disintegration of the tablet to clear the tablet from the gastrointestinal tract after release of the drug has occurred. U.S. Pat. No. 6,340,475 highlights unit oral dosage forms of actives developed by incorporating them into polymeric matrices comprised of hydrophilic polymers that swell upon imbibing water to a size that is large enough to promote retention of the dosage form in the stomach during the fed mode. The polymeric matrix is formed of a polymer selected from the group consisting of poly (ethylene oxide), cellulose, crosslinked polyacrylic acids, xanthan gum and alkyl-substituted celluloses like hydroxymethyl-cellulose, hydroxyethyl-cellulose, hydroxypropyl-cellulose, hydroxypropylmethyl-cellulose and carboxymethyl-cellulose.

Further, gastroretentive systems based on gums have also been developed by some researchers. U.S. Pat. No. 6,635,280 discloses controlled release oral dosage form for highly water soluble drugs comprising one or more polymers forming a solid polymeric matrix which swells upon imbibition of water to a size that is large enough to promote retention of the dosage form in the stomach during the fed mode. Herein the said polymeric matrix is formed of a polymer selected from the group consisting of poly(ethylene oxide), cellulose, alkyl-substituted celluloses, crosslinked polyacrylic acids, and xanthan gum. EP Pat. No. 1745775B1 discloses gastroretentive formulation comprising an active substance granulated with a mixture of a weak gelling agent, a strong gelling agent and a gas generating agent. Herein the strong gelling agent is selected from the group consisting of methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, xanthan gum, guar gum, carrageenan gum, locust bean gum, sodium alginate, agar-agar, gelatin, modified starches, co-polymers of carboxyvinyl polymers, co-polymer of acrylates, co-polymers of oxyethylene and oxypropylene and mixtures thereof. U.S. Patent Application 20040219186A1 provides expandable gastric retention device comprising a gel formed from a polysaccharide, based on xanthan gum or locust bean gum or a combination thereof. U.S. Patent Application 20060177497A1 discloses gellan gum based oral controlled release dosage forms as a platform technology for gastric retention. The dosage form further comprises hydrophilic polymers such as guar gum, hydroxypropyl methylcellulose, carboxymethyl cellulose sodium salt, xanthan gum.

Most of the prior research work thus teaches use of expensive polymers like poly (ethylene oxide) for swelling or Carbopol® for mucoadhesion to develop swelling or mucoadhesive gastroretentive drug delivery systems that delay transit of the dosage form through gastrointestinal tract. A few other researchers describe use of gums of natural origin like locust bean gum; these however tend to have weaker gel strengths than required for gastroretention. Poly (ethylene oxide) is thus the major excipient employed in swelling type of gastroretentive formulations due to its excellent swelling properties. However, poly (ethylene oxide) tends to undergo oxidation with concomitant drop in viscosity which alters its performance. Moreover, poly (ethylene oxide) is very expensive and is a hygroscopic and sticky material requiring special handling precautions and cleaning methodologies. Thus there exists a need to identify excipients for development of a dosage form having delayed transit through gastrointestinal tract which are stable, easy to handle and cost effective. The present invention discloses use of fenugreek fibers for delaying the transit of a dosage form in gastrointestinal tract.

EP1697050 teaches the process of obtaining Fenugreek fibers having a ratio of insoluble to soluble fibers of greater than 0.8, preferably greater than 1.2, more preferably between about 1.2-3, having a viscosity >10,000 cps at 2% w/v and protein content of not more than 10% preferably not more than 8%. This patent also enlists various properties and applications of these fibers having a ratio of insoluble to soluble dietary fibers of greater than 1. Although many pharmaceutical applications of fenugreek fibers are disclosed in this application, it does not teach application of fenugreek fibers for making of delayed transit compositions.

The present inventors have surprisingly found that fenugreek fibers due to its excellent swelling property can be employed for the preparation of delayed transit compositions such as gastroretentive dosage forms. The use of fibers from fenugreek is cost-effective and shows hydration and swelling comparable to those produced by the polymers generally used for providing gastroretentive drug delivery systems. Further fenugreek fibers are stable, possess sufficient gel strength and do not undergo any oxidation thereby maintaining its performance over a period of time. Moreover, it was surprisingly found that the fenugreek fibers also have mucoadhesive properties, potentiating the possibility of gastric retention. Thus this single excipient may provide gastroretention by both the mechanisms of swelling and mucoadhesion, which can be used to provide delivery systems that perform better than the ones employing traditionally used excipients such as polyethylene oxide or Carbopol® or providing gastroretention by a single mechanism that can in some instances lead to failure of the system.

SUMMARY OF THE INVENTION

The present invention provides a composition exhibiting delayed transit through the gastrointestinal tract comprising:
one or more active agents;
fenugreek fiber; and
at least one pharmaceutically acceptable excipient.

OBJECTS OF THE INVENTION

It is an object of the present invention to use Fenugreek fibers for delaying the transit of a dosage form in gastrointestinal tract.

It is further an object of the present invention to provide compositions exhibiting delayed transit through the gastrointestinal tract comprising one or more active agents, Fenugreek fiber and at least one pharmaceutically acceptable excipient.

It is also further, an object of the present invention to provide delayed transit compositions comprising Fenugreek fibers, which are gastroretentive.

It is still further object of the present invention to provide gastroretentive compositions comprising Fenugreek fibers that deliver an active agent near the 'absorption window' at a controlled rate over a period of time.

It is another object of the present invention to provide gastroretentive compositions comprising Fenugreek fibers that deliver an active agent for localized action in the gastrointestinal tract such that the delivery is at a controlled rate over a period of time.

It is yet another object of the present invention to develop gastroretentive compositions comprising Fenugreek fibers with prolonged gastric residence time of at least 2 hours.

It is yet another object of the invention to provide cost effective gastroretentive compositions comprising one or more active agents, Fenugreek fiber and at least one pharmaceutically acceptable excipient.

Yet another object of the present invention is to provide a process for preparation of gastroretentive dosage forms comprising one or more active agents, Fenugreek fiber and at least one pharmaceutically acceptable excipient.

A still further object of the present invention is to provide methods of using compositions comprising one or more active agents, Fenugreek fiber and at least one pharmaceutically acceptable excipient for controlled release and improving bioavailability of active agent.

DETAILED DESCRIPTION OF THE INVENTION

Transit time of orally administered drugs through the gastrointestinal tract is an important factor affecting their absorption and bioavailability. The gastrointestinal transit time of an active agent, in fact, determines the amount of time the agent will remain in contact with its preferred absorptive site. The natural transit time or residence time of food or a pharmaceutical composition through the gastrointestinal tract varies depending on many factors, but approximately the natural stomach residence time varies from about 0 hours to about 2 hours, transit time through the small intestine varies from about 2 to about 4 hours and transit from the large intestine is more than about 10 hours. The residence time in the stomach is more variable and depends upon, amongst other factors, stomach content and timing of ingestion. Any alterations in this gastrointestinal transit time can lead to more complete and more consistent absorption of the active agent.

In the normal digestive process, passage of matter through the stomach is delayed by a physiological condition that is variously referred to as the digestive mode, the postprandial mode, or the "fed mode". The difference between the fed and fasting modes lies in the pattern of gastroduodenal motor activity. In the fasting mode, the stomach exhibits a cyclic activity called the interdigestive migrating motor complex ("IMMC"). This activity occurs in four phases:

Phase I: It lasts 45 to 60 minutes, with the stomach experiencing few or no contractions;

Phase II: It is characterized by sweeping contractions occurring in an irregular intermittent pattern and gradually increasing in magnitude;

Phase III: It consists of intense bursts of peristaltic waves in both the stomach and the small bowel, lasting for about 5 to 15 minutes; and Phase IV: It is a transition period of decreasing activity which lasts until the next cycle begins.

The total cycle time for all four phases is approximately 90 minutes. The greatest activity occurs in Phase III, when powerful peristaltic waves sweep the swallowed saliva, gastric secretions, food particles, and particulate debris, out of the stomach and into the small intestine and colon. Phase III thus serves as an intestinal housekeeper, preparing the upper tract for the next meal and preventing bacterial overgrowth.

The fed mode is initiated by nutritive materials entering the stomach upon the ingestion of food. Once the fed mode is established, the stomach generates 3-4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

In many instances there is a need to alter the gastrointestinal transit of the dosage form in order to achieve the maximum therapeutic benefit of an active agent. The present invention discloses compositions exhibiting delayed transit of one or more active agents through the gastrointestinal (GI) tract. The term "delayed transit through gastrointestinal tract", as used herein, refers to, any increase in the natural transit time or any increase in the natural residence time of an active agent or a composition thereof in the gastrointestinal tract and varies from about 2 hours to about 24 hours, depending on the part of the gastrointestinal tract wherein such a delay occurs, which includes without any limitation, stomach, small intestine or large intestine. According to one embodiment of the present invention, delayed transit of one or more active agents through the gastrointestinal tract is achieved by compositions in the form of gastroretentive dosage forms. Gastroretention of active agents is advantageous in a number of cases. One application wherein the gastroretentive delayed transit compositions of the invention may be advantageous is the administration of drugs having a narrow absorption window wherein their bioavailability and therapeutic effect is enhanced due to gastroretention. Further, some drugs that are absorbed by active transport systems in the upper parts of the gastrointestinal tract, or are poorly soluble at intestinal pH, show improved bioavailability with gastroretentive drug delivery systems. Another application in which use of a gastroretentive drug delivery system may be advantageous is local treatment of diseases of the stomach or duodenum.

Unexpectedly, the inventors of the present invention have found that compositions comprising fenugreek fibers can delay gastrointestinal transit of dosage forms. Such a dosage form comprises one or more active agents, fenugreek fiber and at least one pharmaceutical excipient. In one embodiment of the present invention, the compositions exhibiting delayed transit through gastrointestinal tract comprising one or more active agents, fenugreek fiber and a pharmaceutically acceptable excipient are gastroretentive.

Fenugreek fiber is isolated from Fenugreek or *Trigonella Foenum-graceum* which is an herbaceous plant of the leguminous family and is native to Western Asia. It is one of the oldest cultivated plants and through the ages has found wide applications as a food, a food additive and as a traditional medicine in every region where it has been cultivated. Typically the major constituents of fenugreek seeds have been identified as proteins 20-25%, dietary fiber 45-50% having soluble fiber 18-28% and insoluble fiber 20-30%, fixed fatty acids and essential oils 6-8% and steroidal saponins 2-5%.

The term "fenugreek fiber" as used in the present invention refers to fenugreek dietary fibers that comprise soluble as well as insoluble dietary fibers. The American Association of Cereal Chemists defines dietary fiber comprising soluble and insoluble fibers as the edible part of plants or analogous carbohydrates that are resistant to digestion and absorption in the human small intestine with complete or partial fermentation in the large intestine. Dietary fiber includes polysaccharides, oligosaccharides, lignin, and associated plant substances.

Fenugreek fibers employed for delaying the transit of a dosage form comprise of soluble and insoluble dietary fibers. The soluble dietary fiber is present in an amount from about 5% to about 95% by weight of the fenugreek fiber and the insoluble dietary fiber is present in an amount from about 5% to about 95% by weight of the fenugreek fiber. In one embodiment of the present invention the ratio of insoluble dietary fiber to soluble dietary fiber in the fenugreek fibers employed is about 0.2 to about 5. In further embodiment of the present invention, this ratio is about 0.5 to about 4. In another embodiment of the present invention, this ratio is about 0.8 to 3. In yet another embodiment, this ratio of insoluble dietary fiber to soluble dietary fibers in the fenugreek fibers employed is about 1 to about 3. The fenugreek fiber employed in the compositions of the present invention may in an embodiment have a viscosity greater than 10,000 cps at 2% w/v at 25° C. and protein content of less than 10% by weight of the fiber as described in EP1697050.

The fenugreek fibers employed in the gastroretentive dosage forms of the present invention swell voluminously in presence of gastric contents which leads to an increase in the size of the dosage form such that its passage through the pylorus is precluded. These fibers ensure that at least two dimensions of the dosage forms are greater than 10 mm after swelling within one hour in media simulating gastric environment. Further, these fibers form swollen matrices on contact with the gastric fluids and the integrity of such matrices is maintained over a period that the active agent is released from the delivery system. The swollen polymeric matrix, having achieved sufficient size, remains in the gastric cavity for at least 2 hours irrespective of fed or fasting mode and remains intact long enough till the entire drug is released and/or before substantial dissolution of the matrix occurs. The swelling matrix lowers the accessibility of the gastric fluid to the active agent and thereby reducing the drug release rate. This process results in delivery of the drug to the gastric cavity at a sustained and controlled rate.

It was also surprisingly found that fenugreek fibers, when used in proportions as disclosed by the present invention, also imparts mucoadhesive properties to the dosage form which acts to impart to orally administered dosage forms the ability to resist the strong propulsion forces of the stomach wall. Mucoadhesion acts synergistically with swelling mechanisms to ensure gastric residence of the dosage form.

The compositions of the present invention comprise fenugreek fibers in an amount from about 5% to about 95% by weight of the composition. Further, fenugreek fibers can be incorporated in the compositions of the present invention in any suitable form not restricted to powder and granules.

A suitable active agent for use in the present invention includes those which require delayed transit through the gastrointestinal tract preferably those having an absorption window in the upper part of the gastrointestinal tract, including those therapeutic agents that do not show uniform absorption characteristics throughout the gastrointestinal tract or those having low solubility at high pH values. An active agent according to the present invention includes, but is not limited to, levodopa, methyldopa, carvedilol, hydrochlorothiazide, captopril, orlistat, valsartan, candesartan, eprosartan, irbesartan, losartan, olmesartan, telmisartan, valsartan, pratosartan, acyclovir, metformin, AZT, didanosine, gabapentin, levodopa, oc-methyldopa, baclofen, valacyclovir, nitrofurantoin, ciprofloxacin, amoxicillin, pentoxifylline, prazosin, acyclovir, nifedipine, diltiazem, naproxen, flurbiprofen, ketoprofen, fenoprofen, fentiazac, oestradiol valerate, sulpiride, captopril, cimetidine, zidovudine, nicardipine, terfenadine, salbutamol, carbamazepine, ranitidine, enalapril, simvastatin, fluoxetine, famotidine, ganciclovir, famiciclovir, pentazocine, saquinavir, ritonavir, nelfinavir, thiamphenicol, clarithromycin, azithromycin, ceftazidime, cyclosporine, digoxin, paclitaxel, iron salts, cephalexin, lithium carbonate or citrate, calcium carbonate or citrate, riboflavin, ascorbic acid, folic acid, vitamin E, pravastatin, captopril, benazepril, enalapril, cilazapril, fosinopril, ramipril, albuterol, pirbuterol, furosemide, allopurinol or atenolol.

Further, active agents useful in the treatment of diseases affecting the stomach can be incorporated in the compositions of the present include but are not limited to those suitable for the treatment of H. pylori infection, as well as $H_2$-antagonists and proton pump inhibitors. The following list is intended to provide examples and is not intended to be exclusive: ranitidine, cimetidine, famotidine, nizatidine, omeprazole, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin,flucloxacillin, cefuroxime, cefetamet, cefetrame, cefixime, cefoxitin, ceftazidime, ceftizoxime, latamoxef, cefoperazone, ceftriaxone, cefsulodin, cefotaxime, cephalexin, cefaclor, cefadroxil. cefalothin, cefazolin, cefpodoxime, ceftibuten, aztreonam, tigemonam, erythromycin, dirithromycin, roxithromycin, azithromycin, clarithromycin, clindamycin, paldimycin, lincomycin, vancomycin, spectinomycin, tobramycin, paromomycin, metronidazole, tinidazole, itraconazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol.

Still further, pharmaceutical active agents that tend to be unstable in the lower gastrointestinal tract can be delivered via the gastroretentive compositions of the present invention.

The active agents of the present invention may be present in crystalline, part crystalline or amorphous forms. The crystalline form may have different polymorphs. All different polymorphs, solvates, hydrates, salts, prodrugs, active metabolites, enantiomers, optical isomers, tautomers, racemic mixtures or solubilized forms of the active agent are within the purview of this invention. A combination of one or more of the above listed active agents may be employed, for example to minimize the risk for developing resistance. Depending on the active agent/s used, a therapeutically effective amount thereof may be employed in the compositions of the present invention. The term "effective amount" or "therapeutically effective amount" of an active agent or drug refers to an amount that is nontoxic but sufficient to provide the desired preventive, therapeutic and/or beneficial effect. The active ingredient may be present in an amount from about 1% to about 90% by weight of the composition. An active agent may be included in the compositions in the form of, but not limited to, powder, granules, pellets, beads, or the like.

Further, the compositions of the present invention include at least one pharmaceutically acceptable excipient including, but not limited to, polymers, effervescent couples, superdisintegrants, diluents, release retardants, lubricants, binders, colorants, flavorants, surfactants, pH adjusters, solubilizers, preservatives, stabilizers, anti-adherents or gildants.

The compositions of the present invention may include polymers including, but not limited to, hydrophilic polymers having swelling and or mucoadhesive properties to further promote gastroretention.

Hydrophilic polymers having swelling and or mucoadhesive properties suitable for incorporation in the compositions of present invention include, but are not limited to, polyalkylene oxides; cellulosic polymers; acrylic acid and methacrylic acid polymers, and esters thereof, maleic anhydride polymers; polymaleic acid; poly(acrylamides); poly(olefinic alcohol)s; poly(N-vinyl lactams); polyols; polyoxyethylated saccharides; polyoxazolines; polyvinylamines; polyvinylacetates; polyimines; starch and starch-based polymers; polyurethane hydrogels; chitosan; polysaccharide gums; zein; shellac-based polymers; polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch and polyvinyl alcohol, copolymers and mixtures thereof. The weight percent of the hydrophilic polymer in the composition of the present invention is about 5 to about 90 weight percent, preferably about 10 to about 70 weight percent, and most preferably about 15 to about 50 weight percent.

The compositions of the present invention may contain gas generating agents optionally with an acid source as effervescent couples which aid in the formation of highly porous preferably honeycombed structure that enhances the buoyancy of the formulation. Gas generating agents that may be used in the present invention include, but are not limited to, sodium bicarbonate, sodium glycine carbonate, potassium bicarbonate, ammonium bicarbonate, sodium bisulfite, sodium metabisulfite, and the like. The gas generating agent interacts with an acid source triggered by contact with water or simply with gastric acid to generate carbon dioxide or sulphur dioxide that gets entrapped to form highly porous matrix of the composition and improve its floating characteristics. An acid may be added, including, but not limited to, citric acid and maleic add. In one embodiment the gas generating agent is sodium bicarbonate and the acid source is citric acid.

The compositions of the invention may also comprise at least one super disintegrant including, but not limited to, natural, modified or pregelatinized starch, crospovidone, croscarmellose sodium, sodium starch glycolate, low-substituted hydroxypropyl cellulose, cross-linked sodium or calcium carboxymethyl cellulose. In an embodiment, the super disintegrant employed is crospovidone. The amount of superdisintegrant employed in the composition is about 2% to about 50% by weight of the said dosage form.

The solubilizers which act to increase the instantaneous solubility of the active agent may also be included in the compositions of the present invention. The solubilizer includes, but is not limited to, hydrophilic surfactants or lipophilic surfactants or mixtures thereof. The surfactants may be anionic, nonionic, cationic, and zwitterionic surfactants. Preferably the solubilizer may be selected from PEG-20-glyceryl stearate (Capmul® by Abitec), PEG-40 hydrogenated castor oil (Cremophor® RH 40 by BASF), PEG 6 corn oil (Labrafil® by Gattefosse), lauryl macrogol—32 glyceride (Gelucire®44/14 by Gattefosse) stearoyl macrogol glyceride (Gelucire® 50/13 by Gattefosse), polyglyceryl—10 mono dioleate (Caprol® PEG 860 by Abitec), propylene glycol oleate (Lutrol ® by BASF), Propylene glycol dioctanoate (Captex® by Abitec)Propylene glycol caprylate/caprate (Labrafac® by Gattefosse), Glyceryl monooleate (Peceol® by Gattefosse), Glycerol monolinoleate (Maisine® by Gattefosse), Glycerol monostearate (Capmul® by Abitec), PEG-20 sorbitan monolaurate (Tween 20® by ICI), PEG—4 lauryl ether (Brij 30® by ICI), Sucrose distearate (Sucroester 7® by Gattefosse), Sucrose monopalmitate (Sucroester 15® by Gattefosse), polyoxyethylene-polyoxypropylene block copolymer (Lutrol® series BASF), polyethylene glycol 660 hydroxystearate, (Solutol® by BASF), Soluplus (By BASF), Sodium lauryl sulphate, Sodium dodecyl sulphate, Dioctyl suphosuccinate, L-hydroxypropyl cellulose, hydroxylethylcellulose, hydroxy propylcellulose, Propylene glycol alginate, sodium taurocholate, sodium glycocholate, sodium deoxycholate, betains, polyethylene glycol (Carbowax® by DOW), d-α-tocopheryl polyethylene glycol 1000 succinate (Vitamin E TPGS® by Eastman) or mixtures thereof.

Release retardants suitable for this invention include excipients well known in the pharmaceutical art for their release retarding properties. Examples of such release retardants include, but are not limited to, polymeric release retardants, non-polymeric release retardants or any combinations thereof.

Polymeric release retardants employed for the purpose of the present invention include, but are not limited to, cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. Cellulose derivatives include, but are not limited to, ethyl cellulose, methylcellulose, hydroxypropylmethylcellulose (HPMC), hydroxypropyl cellulose (HPC), hydroxyethyl cellulose, hydroxymethyl cellulose, hydroxyethyl methyl cellulose, carboxymethyl cellulose (CMC), or combinations thereof. Polyhydric alcohols include, but are not limited to, polyethylene glycol (PEG) or polypropylene glycol; or any combinations thereof. Saccharides, gums and their derivatives include, but are not limited to, dextrin, polydextrin, dextran, pectin and pectin derivatives, alginic acid, sodium alginate, starch, hydroxypropyl starch, guar gum, locust bean gum, xanthan gum, karaya gum, tragacanth., carrageenan, acacia gum, arabic gum, fenugreek fibers or gellan gum or the like; or any combinations thereof. Vinyl derivatives, polymers, copolymers or mixtures thereof include, but are not limited to, polyvinyl acetate, polyvinyl alcohol, mixture of polyvinyl acetate (8 parts w/w) and polyvinylpyrrolidone (2 parts w/w) (Kollidon SR), copolymers of vinyl pyrrolidone, vinyl acetate copolymers, polyvinylpyrrolidone (PVP); or combinations thereof. Polyalkylene oxides or copolymers thereof include, but are not limited to, polyethylene oxide, polypropylene oxide, poly (oxyethylene)-poly (oxypropylene) block copolymers (poloxamers) or combinations thereof. Maleic acid copolymers include, but are not limited to, vinylacetate maleic acid anhydride copolymer, butyl acrylate styrene maleic acid anhydride copolymer or the like or any combinations thereof. Acrylic acid polymers and acrylic acid derivatives include, but are not limited to, carbomers, methacrylic acids, polymethacrylic acids, polyacrylates, polymethacrylates or the like or combinations thereof Polymethacrylates, include, but are not limited to, a) copolymer formed from monomers selected from methacrylic acid, methacrylic acid esters, acrylic acid and acrylic acid esters c) copolymer formed from monomers selected from ethyl acrylate, methyl methacrylate and trimethylammonioethyl methacrylate chloride, or the like or any combinations thereof.

Non-polymeric release retardants employed for the purpose of the present invention include, but are not limited to, fats, oils, waxes, fatty acids, fatty acid esters, long chain monohydric alcohols and their esters or combinations thereof. In an embodiment, non-polymeric release retardants employed in the present invention, include, but are not limited to, Cutina (hydrogenated castor oil), Hydrobase (hydrogenated soybean oil), Castorwax (hydrogenated castor oil), Croduret (hydrogenated castor oil), Carbowax, Compritol (glyceryl behenate), Sterotex (hydrogenated cottonseed oil), Lubritab (hydrogenated cottonseed oil), Apifil (wax yellow), Akofine (hydrogenated cottonseed oil), Softisan (hydrogenated palm oil), Hydrocote (hydrogenated soybean oil), Corona (lanolin), Gelucire (macrogolglycerides lauriques), Precirol (glyceryl palmitostearate), Emulcire (cetyl alcohol), Plurol diisostearique (polyglyceryl diisostearate), and Geleol (glyceryl stearate), and mixtures thereof.

The amount of release retardant relative to the active agent may vary depending on the release rate desired, nature of the retardants and their physicochemical characteristics. The amount of the release retardant in the dosage form generally varies from about 5% to about 50% by weight of the composition. Preferably, the amount of release retardant varies from about 5% to about 30% by weight of the dosage form.

The compositions of the present invention typically may also include other pharmaceutically acceptable excipients. As is well known to those skilled in the art, pharmaceutical excipients are routinely incorporated into solid dosage forms. This is done to ease the manufacturing process as well as to improve the performance of the dosage form. The present invention may include one or more diluents in an amount within the range of from about 0% to about 90% by weight such as, but not limited to, lactose, sugar, corn starch, modified corn starch, mannitol, sorbitol, inorganic salts such as calcium carbonate, dicalcium phosphate and/or cellulose derivatives such as wood cellulose and microcrystalline cellulose. A glidant may be used to improve powder flow properties prior to and during tableting and to reduce caking. Suitable glidants include, but are not limited to, colloidal silicon dioxide, talc, magnesium trisilicate, powdered cellulose, talc, tribasic calcium phosphate and the like. The composition may include lubricants such as, but not limited to, magnesium stearate, stearic acid, palmitic acid, calcium stearate, talc, polyethylene glycol, colloidal silicon dioxide, sodium stearyl fumarate, carnauba wax and the like or any combinations thereof in an amount from about 0.2% to about 8% by weight of the composition. The compositions of the present invention may further include suitable binders selected from but not limited to starch, polyethylene glycol, polyvinylpyrrolidone, hydroxypropyl methyl cellulose and hydroxypropylcellulose and natural and synthetic gums. The compositions of the present invention may also include stabilizers such as, but not limited to, benzoic acid, sodium benzoate, citric acid, and the like. Examples of surfactants include, but are not limited to, sodium docusate, glyceryl monooleate, polyethylene alkyl ether, polyoxyethylene sorbitan fatty acid ester, sodium lauryl sulfate, sorbic acid, sorbitan fatty acid ester, and mixtures thereof.

The gastroretentive compositions of the present invention may be in a form such as, but not limited to, a monolithic or multi-layered dosage form or in-lay system. In one embodiment of the present invention the gastroretentive compositions are in the form of a bilayered or trilayered solid dosage form. In an illustrative embodiment, a solid pharmaceutical composition in the form of an expanding bilayered system for oral administration is adapted to deliver an active pharmaceutical agent from a first layer immediately upon reaching the gastrointestinal tract, and to deliver a further pharmaceutical agent which may be same or different from a second layer, in a modified manner over a specific time period. The second layer containing fenugreek fibers provides expanding nature for the dosage system, thereby making the dosage system have greater retention in the stomach.

In a further illustrative embodiment a solid pharmaceutical composition for oral administration contains two layers: one comprising of active ingredient along with a suitable release retardant and the other layer comprising fenugreek fibers in combination with other excipients.

In another embodiment of the present invention, a solid pharmaceutical composition for oral administration contains an in-lay system which a specialized dosage form comprising an active agent containing tablet which is placed in another tablet comprising of excipients that ensure gastric retention. In this system the active agent containing tablet is small and is covered from all sides except at least one side with a blend of excipient comprising fenugreek dietary fibers that ensures gastric retention.

In yet another embodiment of the present invention, the dosage form may be optionally coated. Surface coatings may be employed for aesthetic purposes or for dimensionally stabilizing the compressed dosage form or for retarding the drug release. The surface coating may be any conventional coating which is suitable for enteral use. The coating may be carried out using any conventional technique employing conventional ingredients. A surface coating can for example be obtained using a quick-dissolving film using conventional polymers such as, but not limited to, hydroxypropyl methyl cellulose, hydroxypropyl cellulose, carboxymethyl cellulose, polyvinyl alcohol, poly methacrylates or the like.

The compositions of the present invention release the active agent having an absorption window in the upper part of the gastrointestinal tract in a controlled manner for improved absorption and efficacy compared to other non-gastroretentive controlled release dosage forms. A controlled release composition according to the present invention is one that achieves slow release of a drug over an extended period of time, thereby extending the duration of drug action over that achieved by conventional delivery. In an embodiment, the compositions of the present invention maintain drug concentration in the blood within the therapeutic range for 2 hours or more. In another embodiment the gastroretentive dosage form of the present invention comprising fenugreek fibers is retained in the stomach for at least 2 hours. In yet another embodiment the gastroretentive dosage form of the present invention is retained in the stomach for about 2 to about 12 hours. In a further embodiment the composition of the present invention exhibits controlled release of active agent over a period of up to about 24 hours.

In another embodiment, the present invention provides controlled release gastroretentive compositions in the form of solid oral dosage forms, wherein the said composition is formulated by compressing or compacting powder, granules, pellets, beads, compacts, shear form particles, floss, or the like, or combinations thereof into a tablet or minitablet or caplet or filling the composition into a capsule. In an embodiment, the composition in the form of a tablet is prepared by either direct compression (slugging), wet granulation, dry granulation and extrusion/melt granulation. The granulation technique is either aqueous or non-aqueous. Tablet may vary in shape including, but not limited to oval, triangle, almond, peanut, parallelogram, pentagonal. The final dosage form may also be coated with suitable coating materials for either functional or non-functional use known to those skilled in the art of formulation development without hindering the release of therapeutic agent from the gastro retentive dosage form. Further, an active agent can also be present in the coating.

Further, the present invention also provides a process for preparing a composition in the form of a monolithic gastroretentive dosage form exhibiting delayed transit through gastrointestinal tract comprising blending active agent, fenugreek fibers and at least one pharmaceutically acceptable excipient and compressing the blend to form matrix tablets. In a further embodiment, the present invention also provides a process for preparing a composition in the form of a bilayered gastroretentive dosage form exhibiting delayed transit through gastrointestinal tract comprising the steps of: (a) blending active agent, at least one release retardant and lubricant to form drug layer; (b) blending fenugreek fibers, at least one lubricant and at least one pharmaceutically acceptable excipient to form gastrorentive layer; and (c) compressing the drug layer of step (a) and the gastrorentive layer of step (b) into bilayer tablets.

Further, in another embodiment of the present invention, the compositions are in the form of multiparticulates including, but not limited to, pellets, microspheres, microcapsules, having prolonged transit in the intestine to effectively deliver active agents that require longer retention times in the intestinal tract. In one embodiment, multiparticulate systems prepared employing fenugreek fibers are bioadhesive or mucoadhesive. Such a bioadhesive system delays gastrointestinal transit. In another embodiment, the compositions of the present invention, in the form of multiparticulates such, but not limited to, pellets, microspheres, microcapsules, are gastroretentive. These multiparticulate systems may be prepared by methods including, but not limited to, pelletization, granulation, spray drying, spray congealing and the like.

In yet another embodiment, the present invention discloses use of fenugreek fiber for the manufacture of a medicament that exhibits delayed transit through the gastrointestinal tract. In another embodiment the present invention discloses use of fenugreek fiber for the manufacture of a medicament for gastroretention of one or more active agents. Still another embodiment of the present invention discloses a method of using compositions of the present invention employing fenugreek fibers comprising administering to a subject in need thereof an effective amount of the composition depending on the active agent used. In one embodiment the present invention discloses a method of preparing compositions exhibiting delayed transit through the gastrointestinal tract comprising incorporating fenugreek fibers in the compositions along with one or more active agents and at least one pharmaceutically acceptable excipient. In another embodiment the present invention discloses method of preparing compositions in the form of a gastroretentive dosage form exhibiting delayed transit through the gastrointestinal tract comprising incorporating fenugreek fibers in the compositions along with one or more active agents and at least one pharmaceutically acceptable excipient. According to a further aspect of the invention there is provided a method of treatment or prophylaxis of a disease which comprises administration of a composition of the invention exhibiting delayed transit through the gastrointestinal tract including one or more active agent which is effective against said disease to a patient in need of such treatment.

While the present invention has been described in terms of its specific embodiments, certain modifications and equivalents will be apparent to those skilled in the art and are intended to be included within the scope of the present invention.

The invention is further illustrated by the following examples, which are for illustrative purposes and should not be construed as limiting the scope of the invention in any way.

EXAMPLES

Example 1

Comparative Evaluation of the Swelling Index of Fenugreek Fibers and Carbopol®974P The swelling index is the volume in millilitres occupied by 1 gram of test material after it has swollen in an aqueous liquid for 4 h. The swelling index of fenugreek fibers was compared against that of Carbopol®974P using the method laid down in European Pharmacopoeia 6.0. The method involved placing 1.0 g of the test material in a 25 ml ground-glass stoppered cylinder, which are shaken vigorously every 10 minutes for 1 hour and then allowed to stand for 3 hours. The volume occupied by the test material is measured, including any adhering mucilage. The results as depicted in the table beneath clearly indicate that the swelling index of fenugreek fibers is better than the commonly used Carbopol®974P. Thus fenugreek fiber can act as a better gastroretentive excipient.

| Test material | Swelling Index |
|---|---|
| Fenugreek fiber | 22.2 |
| Carbopol ®974P | 15.1 |

Example 2

Evaluation of Mucoadhesive Property of Fenugreek Fibers

A composition comprising 10% fenugreek fibers was evaluated against a formulation having 10% sodium carboxy methyl cellulose (Blanose 7HFPH), that is commonly used for mucoadhesive purposes. The mucoadhesive property was evaluated using a modified analytical balance using Blanose HFPH film as a substrate. The composition was wetted with addition of small amounts of water on it with the help of hypodermic syringe. A 20 seconds contact time was allowed between mucosal film and the composition. After the contact time, the balance was switched on and weights were added in small increments. The weight required to detach the dosage form from the mucosal film was taken as reading for mucoadhesion. The evaluation was carried out in triplicate. The composition with 10% fenugreek fibers of the said invention showed excellent mucoadhesive property as compared to the composition with 10% Blanose 71HFPH.

| Amount of material in composition (%) | Force of detachment (gm) | | | | |
|---|---|---|---|---|---|
| Readings | I | II | III | Mean | SD |
| Blanose 7HF PH (10) | 2.7 | 3 | 2.65 | 2.78333 | 0.189 |
| Fenugreek fiber (10) | 8.75 | 9 | 11.76 | 9.83667 | 1.670 |

Example 3

Gastroretentive Delivery System of Metformin Hydrochloride using Fenugreek Fiber

| Composition | mg/tab |
|---|---|
| Metformin hydrochloride | 500 |
| Fenugreek fiber | 300 |
| Microcrystalline cellulose, USP | 190 |
| Colloidal silicon dioxide, USP | 5 |
| Magnesium stearate, USP | 5 |
| Total | 1000 |

Fenugreek fiber, microcrystalline cellulose and colloidal silicon dioxide were sieved and mixed with metformin hydrochloride. The blend was directly compressed to get a matrix tablet formulation.

Dissolution Study: Dissolution was carried out for 12 hours in 0.1N HCl
Dissolution Test Apparatus: USP Type II
Temperature: 37.0±0.5° C.
Dissolution Medium: 900 ml 0.1N HCl
Rpm: 50

| Formulation Details Time point (hrs) | Formulation with Fenugreek fiber % Drug Release |
|---|---|
| 1 | 37.2 |
| 2 | 52.5 |
| 4 | 71.7 |
| 6 | 84.4 |
| 8 | 95.2 |

The gastroretentive formulation with Fenugreek fiber exhibited release of metformin hydrochloride over 8 hours.

Example 4

Gastroretentive Delivery System of Metformin Hydrochloride using Combination of Fenugreek Fiber and Sodium Carboxy Methyl Cellulose

| Composition | mg/tab |
|---|---|
| Metformin hydrochloride | 500 |
| Copovidone, USP | 5 |
| Sodium carboxy methyl cellulose, USP | 100 |
| Fenugreek fiber | 350 |
| Microcrystalline cellulose, USP | 40 |
| Magnesium stearate, USP | 5 |
| Total | 1000 |

Copovidone was dissolved in de-mineralized water forming a solution and metformin hydrochloride was granulated using this solution. Granules thus obtained were dried in fluidized bed dryer to achieve LOD of 1-4%. These granules were then sieved and mixed with remaining excipients. The blend was lubricated and compressed into tablets.

Example 5

Gastroretentive Acyclovir Formulation using Fenugreek Fiber

| Ingredients | mg/tab |
|---|---|
| Acyclovir | 200 |
| Poloxamer 407, USP | 40 |
| Fenugreek fiber | 240 |
| Crospovidone, USP | 280 |
| Povidone, USP | 50 |
| Dextrate dihydrate, USP | 220 |
| Magnesium stearate, USP | 10 |
| Total | 1040 |

Acyclovir was mixed with molten Poloxamer 407. This mixture was then blended with fenugreek fiber, crospovidone, dextrate dihydrate. The blend was further granulated with povidone. The granules were dried and lubricated with magnesium stearate. The tablets were compressed as matrix tablets.

Example 6

Gastroretentive Bilayer Tablets of Acyclovir with Fenugreek Fiber

Acyclovir bilayer tablet was formulated using fenugreek fiber as gastroretentive layer and another layer as immediate release layer.
Composition of Acyclovir Gastroretentive Layer

| Ingredient | mg/tab |
|---|---|
| Acyclovir | 200 |
| Stearoyl macrogol glyceride, Ph. Eur. | 40 |
| Fenugreek fiber | 240 |
| Crospovidone, USP | 280 |
| Povidone, USP | 50 |

| Ingredient | mg/tab |
|---|---|
| Dextrate dihydrate, USP | 220 |
| Magnesium stearate, USP | 10 |
| Weight of gastroretentive layer | 1040 |

Procedure

Acyclovir was mixed with molten stearoyl macrogol glyceride. This mixture was then blended with fenugreek fiber, crospovidone and dextrate dihydrate. This blend was further granulated with povidone. The granules were dried and lubricated with magnesium stearate.

Composition of Acyclovir Immediate Release Layer

| Ingredients | mg/tablet |
|---|---|
| Acyclovir | 50 |
| Microcrystalline cellulose, USP | 52.5 |
| Povidone, USP | 2 |
| Sodium starch glycolate, USP | 5 |
| Magnesium stearate, USP | 0.5 |
| Weight of immediate release layer | 110 |

Procedure

The immediate release layer was prepared by granulating the drug along with microcrystalline cellulose using povidone and lubricating with sodium starch glycolate and magnesium stearate.

Gastroretentive layer and immediate release layer of acyclovir were compressed together to form a bilayer tablet.

Example 7

Gastroretentive Valsartan Bilayer Tablets using Fenugreek Fiber

Composition of Drug Layer

| Ingredients | mg/tab |
|---|---|
| Valsartan Granules | 200 |
| Hydroxy propyl cellulose, USP | 40 |
| Microcrystalline cellulose, USP | 80 |
| Colloidal silicon dioxide, USP | 5 |
| Magnesium stearate, USP | 5 |
| Weight of drug layer | 330 |

Valsartan granules prepared by granulation with povidone were mixed with hydroxyl propyl cellulose, microcrystalline cellulose and colloidal silicon dioxide. The mass thus formed was lubricated as drug layer for the bilayer formulation.

Composition of Gastroretentive Layer

| Ingredients | mg/tab |
|---|---|
| Fenugreek fiber | 325 |
| Crospovidone, USP | 130 |
| Povidone, USP | 25 |
| Lactose monohydrate, USP | 29 |
| Microcrystalline cellulose, USP | 30 |
| Sodium bicarbonate, USP | 45 |

| Ingredients | mg/tab |
|---|---|
| Citric acid, USP | 18 |
| Magnesium stearate, USP | 6 |
| Weight of gastroretentive layer | 608 |

Fenugreek fibers along with part of crospovidone were granulated using povidone solution in Isopropyl alcohol and water to get granular mass. The excipients like lactose, microcrystalline cellulose, sodium bicarbonate, citric acid and remaining amount of crospovidone were sifted and blended with fenugreek fiber granules and lubricated using magnesium stearate.

Bilayer Tablet Formulation

Valsartan layer and gastroretentive layer were compressed in the form of bilayer tablet and swelling of the tablets was studied.

Swelling and Floating Evaluation

| Width in 1 hr. in 0.1N HCl (mm) | 12.3 mm |
|---|---|
| Floating time | 1 min 10 sec |

Example 8

Comparative Evaluation of Gastroretentive Valsartan Bilayer Tablets using Polyox WSR 303 and Fenugreek Fibers Formulation explained under example 8A (Polyox®) was used as control formulation and compared for swelling property of example 8B where fenugreek fiber was used in place of Polyox® WSR 303.

Composition of Drug Layer

Valsartan drug layer of the composition as described in Example 7 was used for formulation of gastroretentive bilayer tablets of this example.

Composition of Gastroretentive Layer

| Formulation Details Ingredients | Example 8A Mg/tab | Example 8B mg/tab |
|---|---|---|
| Fenugreek fiber | — | 200 |
| Polyethylene oxide, USP (Polyóx ® WSR 303) | 200 | — |
| Hydroxy propyl methyl cellulose, USP | 200 | 200 |
| Hydroxy ethyl cellulose, USP | 100 | 100 |
| Crospovidone, USP | 200 | 200 |
| Povidone, USP | 35 | 35 |
| Lactose monohydrate, USP | 45 | 45 |
| Microcrystalline cellulose, USP | 45 | 45 |
| Sodium bicarbonate, USP | 45 | 45 |
| Citric acid, USP | 18 | 18 |
| Magnesium stearate, USP | 8 | 8 |
| Weight of gastroretentive layer | 896 | 896 |

Procedure for Gastroretentive Layer Preparation for Example 8 A

Povidone was dissolved in IPA: water mixture with overhead stirring. Polyox® WSR 303 along with other ingredients was passed through the sieve and dry mixed in rapid mixer granulator. The binder solution was added to the dry mix and the mass was granulated and subsequently dried in a fluidized bed dryer to get desired loss on drying. Sized dried granules were blended with other excipients like lactose, microcrystalline cellulose, sodium bicarbonate and citric acid and then lubricated using magnesium stearate.

Procedure for Gastroretentive Layer Preparation for Example 8 B

Similar procedure as mentioned above was employed in case of fenugreek fibers.

Bilayer Tablet Formulation:

Drug layer and gastroretentive layer as explained under 8A and 8B were compressed in the form of bilayer tablet and swelling of the tablet formulations was studied.

Swelling and Floating Evaluation:

| Evaluation parameter | Example 8A | Example 8B |
|---|---|---|
| Width in 1 hr in 0.1N HCl (mm) | 12.01 | 11.86 |
| Swelling in simulated gastric fluid | 40% | 38% |
| Floating in 0.1N HCl | 50 sec | 40 sec |
| Strength of gastroretentive layer | Intact for more than 24 hours | Intact for more than 24 hours |

As evident from the data, it was observed that the gastroretentive formulation with Polyox® WSR 303 (Example 8A) and fenugreek fiber (Example 8B) exhibited comparable swelling and floating characteristics.

The invention claimed is:

1. An orally administrable composition in a gastroretentive dosage form comprising a mixture of:
   (a) a therapeutically effective amount of one or more pharmaceutically active agents;
   (b) fenugreek fibers comprising insoluble and soluble dietary fibers in a ratio of insoluble to soluble fibers of about 0.2:1 to about 5:1, wherein the fenugreek fibers are present in an amount of about 5% to about 95% by weight of said dosage form; and
   (c) at least one pharmaceutically acceptable excipient, wherein said dosage form is a form which
   (i) upon contacting with a solution of 0.1N HCl swells such that at least two dimensions of the swollen dosage form are greater than 10 mm within one hour and the swollen dosage form maintains integrity in said solution for at least 2 hours, and (ii) upon oral administration of the dosage form to a human patient, the dosage form swells to a size exceeding the pyloric diameter in the fed mode thereby promoting retention of the dosage form in the stomach during the fed mode.

2. The composition of claim 1 wherein said soluble dietary fiber is present in an amount of about 5% to about 95% by weight of said fenugreek fiber.

3. The composition of claim 1 wherein said insoluble dietary fiber is present in an amount of about 5% to about 95% by weight of said fenugreek fiber.

4. The composition of claim 1 wherein said fenugreek fiber has a ratio of insoluble to soluble dietary fibers of between about 0.8:1 to about 3:1.

5. The composition of claim 4 wherein said fenugreek fiber has a ratio of insoluble to soluble dietary fibers of between about 1:1 to about 3:1.

6. The composition of claim 1 wherein said active agent is a pharmaceutically active agent having an absorption window in the gastrointestinal tract, having non-uniform absorption characteristics throughout the gastrointestinal tract, having low solubility at high pH values, having local action in the gastrointestinal tract, having instability in the lower gastrointestinal tract or requiring longer duration in the intestine.

7. The composition of claim 6 wherein said one or more pharmaceutically active agents is selected from the group consisting of levodopa, methyldopa, carvedilol, hydrochlorothiazide, captopril, orlistat, valsartan, candesartan, eprosartan, irbesartan, losartan, olmesartan, telmisartan, valsartan, pratosartan, acyclovir, metformin, AZT, didanosine, gabapentin, levodopa, α-methyldopa, baclofen, valacyclovir, nitrofurantoin, ciprofloxacin, amoxicillin, pentoxifylline, prazosin, acyclovir, nifedipine, diltiazem, naproxen, flurbiprofen, ketoprofen, fenoprofen, fentiazac, oestradiol valerate, sulpiride, captopril, cimetidine, zidovudine, nicardipine, terfenadine, salbutamol, carbamazepine, ranitidine, enalapril, simvastatin, fluoxetine, famotidine, ganciclovir, famiciclovir, pentazocine, saquinavir, ritonavir, nelfinavir, thiamphenicol, clarithromycin, azithromycin, ceftazidime, cyclosporine, digoxin, paclitaxel, iron salts, cephalexin, lithium carbonate or citrate, calcium carbonate or citrate, riboflavin, ascorbic acid, folic acid, vitamin E, pravastatin, captopril, benazepril, enalapril, cilazapril, fosinopril, ramipril, albuterol, pirbuterol, furosemide, allopurinol, atenolol, ranitidine, cimetidine, famotidine, nizatidine, omeprazole, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixime, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycin, vancomycin, spectinomycin, tobramycin, paromomycin, metronidazole, tinidazole, itraconazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol, metoprolol, and combinations thereof.

8. The composition of claim 1 wherein said pharmaceutically acceptable excipient is a polymer, effervescent couple, superdisintegrant, diluent, release retardant, lubricant, granulating aid, colorant, flavorant, pH adjuster, solubilizer, preservative, stabilizer, anti-adherent or glidant material.

9. The composition of claim 8, wherein the superdisintegrant material is selected from the group consisting of crospovidone, croscarmellose sodium, sodium starch glycolate, substituted hydroxypropyl cellulose, cross-linked calcium carboxymethyl cellulose, and combinations thereof.

10. The composition of claim 1, wherein said dosage form exhibits controlled release of said one or more pharmaceutically active agents over a period of up to about 24 hours.

11. An orally administrable composition in a gastroretentive dosage form comprising:
   (a) a first layer comprising a therapeutically acceptable amount of one or more pharmaceutically active agents and at least one release retardant material; and
   (b) a gastroretentive second layer in contact with the first layer, comprising (i) fenugreek fibers comprising insoluble and soluble dietary fibers in a ratio of insoluble to soluble fibers of about 0.2:1 to about 5:1, wherein the fenugreek fibers are present in an amount of about 5% to about 95% by weight of said dosage form and (ii) one or more additional excipients, wherein said dosage form is a form which (i) upon contacting with a solution of 0.1N HCl swells such that at least two dimensions of the swollen dosage form are greater than 10 mm within one hour and the swollen dosage form maintains integrity in said solution for at least 2 hours, and (ii) upon oral administration of the dosage form to a human patient, the dosage form swells to a size exceeding the pyloric diameter in the fed mode thereby promoting retention of the one or more pharmaceutically acceptable active agents in the stomach during the fed mode.

12. The composition of claim 11 wherein the gastroretentive second layer does not contain a pharmaceutically active agent.

13. An orally administrable composition in a gastroretentive dosage form comprising:

(a) therapeutically effective amount of one or more pharmaceutically active agents;

(b) fenugreek fibers comprising insoluble and soluble dietary fibers in a ratio of insoluble to soluble fibers of about 0.2:1 to about 5:1, wherein the fenugreek fibers are present in an amount of about 5% to about 95% by weight of said dosage form; and (c) at least one pharmaceutically acceptable excipient;

wherein said dosage form is a form which (i) upon contacting with a solution of 0.1N HCl swells such that at least two dimensions of the swollen dosage form are greater than 10 mm within one hour and the swollen dosage form maintains integrity in said solution for at least 2 hours, and (ii) upon oral administration of the dosage form to a human patient, the dosage form swells to a size exceeding the pyloric diameter in the fed mode thereby promoting retention of the one or more pharmaceutically active agents in the stomach during the fed mode.

* * * * *